United States Patent [19]

Maasböl et al.

[11] 4,279,914

[45] Jul. 21, 1981

[54] THROMBOCYTE AGGREGATION INHIBITING COMPOSITION AND METHODS

[75] Inventors: Alfred G. Maasböl, Hamburg, Fed. Rep. of Germany; Alexander K. Sim, Falkirk, Scotland

[73] Assignees: Hermann Gottfried Schnabel Fa.; Karl O. Helm, both of Hamburg, Fed. Rep. of Germany

[21] Appl. No.: 64,540

[22] Filed: Aug. 7, 1979

Related U.S. Application Data

[63] Continuation of Ser. No. 895,717, Apr. 12, 1978, abandoned.

[30] Foreign Application Priority Data

Apr. 18, 1977 [DE] Fed. Rep. of Germany ....... 2717001

[51] Int. Cl.$^3$ .................... A61K 31/47; A61K 31/485
[52] U.S. Cl. .................................... 424/258; 424/260
[58] Field of Search .............................. 424/258, 260

[56] References Cited

U.S. PATENT DOCUMENTS

| 2,951,013 | 8/1960 | Dengel | 424/258 |
| 3,795,675 | 3/1974 | Laguzzi | 424/258 |
| 3,810,987 | 5/1974 | Saari | 424/258 |
| 3,823,234 | 7/1974 | Mauvernay | 424/260 |
| 3,910,927 | 10/1975 | Kreighbaum et al. | 424/258 |
| 4,018,927 | 4/1977 | Voorhees | 424/260 |
| 4,080,456 | 3/1978 | Seidelmann et al. | 424/258 |

OTHER PUBLICATIONS

The Pharmacological Basis of Therapeutics-pp. 279-280 (1966).
Chem. Abst. 58 4941(h), 1963–Vernadakis et al.
Chem. Abst. 61 9928(g), 1964–Donev.

*Primary Examiner*—Douglas W. Robinson
*Attorney, Agent, or Firm*—Michael J. Striker

[57] ABSTRACT

Platelet aggregation inhibiting compositions containing as active agent at least one compound selected from the group consisting of tetrahydroxyaporphine, glaucine containing 50 to 100% l-glaucine, and the physiologically acceptable salts and N-alkyl ammonium salts thereof are disclosed, as is a method for inhibiting platelet aggregation by administration of effective dosages of such compounds admixed with suitable carriers.

5 Claims, No Drawings

THROMBOCYTE AGGREGATION INHIBITING COMPOSITION AND METHODS

CROSS-REFERENCE TO RELATED APPLICATION

This application is a continuation of Ser. No. 895,717 filed Apr. 12, 1978 now abandoned.

The invention relates to medicines which have anti-thrombotic effects, and to their manufacture.

It is known that papaverine has a certain anti-thrombotic effect, but this substance, when injected in effective concentration has such strong side effects on the vessels that it is practically not applicable for this purpose.

The problem tackled in the present invention is to provide a medicine which, used at the lowest possible active substance concentration, produces an anti-thrombotic effect largely free from undesired side effects.

In solving this problem the anti-thrombotic medicines according to the present invention are characterized by a therapeutically effective content of one or more compounds of the general structure:

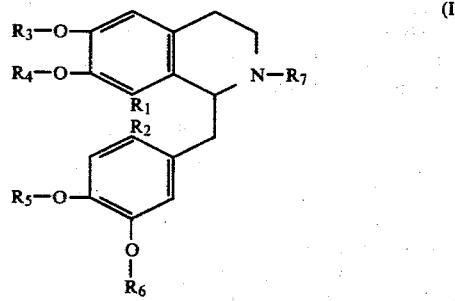

in which $R_1$ and $R_2$ are hydrogen atoms or, taken together, represent a carbon-carbon bond, whereas $R_3$ to $R_7$ are hydrogen atoms independent of each other or low-molecular alkyl groups each containing up to four carbon atoms and/or their salts derived from physiologically unobjectionable organic or inorganic acids or N-alkyl substituted quarternary compounds said compound in case of glaucine containing l-glaucine.

Even at active substance concentrations far below what is necessary for papaverine, the medicines according to the present invention have a pronounced anti-thrombotic effect and are largely free from the side effects which occur when papaverine is used.

Among the compounds represented by the structural formula (I) there are, in particular, tetrahydropapaverine, tetrahydropapaveroline, laudanosine, laudanosoline, tetrahydroxyaporphine, tetrahydroxynoraporhine, l-glaucine and d,l-glaucine and their salts with physiologically unobjectionable inorganic or organic acids and the corresponding quarternary ammonium methohalides.

Advantageous practical forms of the medicine are described in the subsidiary claims.

The present invention also includes the application of compounds represented by Formula (I) and/or their salts derived from physiologically unobjectionable organic or inorganic acids or N-alkyl substituted quarternary ammonium compounds in the manufacture of, in particular, orally administerable medicines with anti-thrombotic effects.

In what follows the manufacture will be described of the active substances used in the medicines according to the invention, on the basis of several examples.

EXAMPLE 1

For making laudanosine there was added to 225 g (0.6 Mol) of papaverine hydrochloride in 2 liters of 50% aqueous methyl alcohol a solution of 30 g sodium hydroxide in 300 ml water, the addition being made slowly. The resulting precipitate was filtered off and dried for 20 hours at 60° C. The product was 201 g of papaverine base with a melting point of 144° to 146° C. (yield 98%).

200 g (0.6 Mol) of the papaverine base was dissolved in 200 ml of methyl alcohol. To the solution there was added 120 ml of methyl iodide and the whole heated to boiling during 6 hours. After cooling, the crystalline product was filtered off and dried. The product was 280 g of papaverine methiodide with a melting point of 127° to 129° C. (yield 97%).

200 g (0.4 Mol) of the papaverine methiodide was suspended in 2 liters of a 10% aqueous methyl alcohol and to this mixture there was added sodium borhydride until complete solution was obtained and the yellow-orange colouration has disappeared. The resulting solution was poured into 12 liters of water and the resulting white precipitate was filtered off and dried. The product was 230 g of laudanosine with a melting point of 113° to 115° C. (yield 78%).

EXAMPLE 2

To make laudanosoline hydrobromide 121 g (0.34 Mol) of laudanosine was heated in 600 ml of 40% hydrobromic acid for about 10 hours, until all the methyl bromide was removed. After cooling the solution, the crystalline product was separated. The product was 100 g of laudanosoline hydrobromide with a melting point of 230° C. (yield 77%).

EXAMPLE 3

To make tetrahydroxyaporphine hydrochloride, 98 g (0.26 Mol) of laudanosoline hydrobromide was dissolved in 1.2 liters of a 50% aqueous methyl alcohol at 80° C. After complete solution, the solution was cooled down to 6° C. by adding ice, after which there was added a filtered solution, which had also been cooled to 6° C., of 100 g (0.62 Mol) of iron (III) chloride in 500 ml of 50% aqueous methyl alcohol. After one minute there was added 1.5 liters of concentrated hydrochloric acid and the solution was allowed to stand at room temperature. The precipitated grey-brown crystals were filtered off, washed with acetone and dried. The product was 43 g of tetrahydroxyaporphine hydrochloride showing a melting point of 242° to 244° C. (yield 50%).

EXAMPLE 4

For making d,l-glaucine hydrobromide, 6 g (0.018 Mol) of tetrahydroxyaporphine hydrochloride was dissolved with warming in 840 ml of methyl alcohol. In a separate operation, 21.6 g (0.126 Mol) of trimethylphenylammonium chloride in methyl alcohol was reacted with a solution of 8.5 g (0.15 Mol) of KOH in methyl alcohol. After filtering off the precipitated potassium chloride, the filtrate was made up to 840 ml with methyl alcohol. The two solutions were then mixed together slowly under a protective gas, and added slowly in the course of 6 hours to anisol heated to 110° C., the methyl alcohol distilling off. After completion of the addition the solution was cooled and a black, amorphous residue was removed by filtering. The resulting dark green filtrate was evaporated under vacuum until dry. To the residue there was added 5 ml ethanol 15 ml hydrobromic acid and 20 ml of ethyl acetate. From the resulting mixture a product crystallized out and was filtered off and dried. The product was 5.5 g of d,l-glaucine hydrobromide with a melting point of 235° C. (with decomposition) (yield 67%).

EXAMPLE 5

A thin-layer chromatograph showed that the d,l-glaucine hydrobromide made by the process of Example 4 contained about 10% of 1-(N,N-dimethylaminoethyl)-3,4,6,7-tetramethyoxyphenanthrene. 60 g of this d,l-glaucine hydrobromide was dissolved in 200 ml of 50% aqueous ethanol and reacted with an excess of 8.5 g of potassium hydroxide in 50 ml of water.

The resulting mixture was shaken with about 500 ml of chloroform to extract the free d,l-glaucine base. The separated organic phase was dried over anhydrous sodium sulphate and filtered. After evaporating off the solvent 50 mg of an oily residue was obtained and this was recrystallized from 75 ml of ethyl acetate. After filtering and drying there was obtained 30.4 g of d,l-glaucine base showing a melting point of 128° to 130° C. After repeated recrystallization from further 100 ml portions of ethyl acetate, there was obtained 25.15 g of d,l-glaucine base with a melting point of 138° to 140° C. By making a thin-layer chromatograph it was determined that this contained less than 0.1% of impurities.

After recrystallizing the combined residues from ethyl alcohol there was obtained about 5 g of 1-(N,N-dimethylaminoethyl)-3,4,6,7-tetramethoxyphenanthrene with a melting point of 248° to 250° C. and a molecular weight, determined by mass spectrometry, of 369. NMR spectrum: 9.13(s,1), 7.88(d,1), 7.66(d,1), 7.46(s,2), 3.97(s,3), 3.93(s,6), 3.86(s,3), 3.44–3.14(m,4), 2.73(s,3), 2.52(s,3).

To separate the isomers, 5.09 g (0.014 Mol) of d,l-glaucine was dissolved in 70 ml of ethyl alcohol and the solution reacted with a solution of 2.2 g (0.014 Mol) of d-tartaric acid in 70 ml of ethyl alcohol (50° C.). Slow cooling resulted in a fine crystalline precipitate which was filtered off, washed with ether and dried. The product was 3.6 g of l-glaucine-d-bitartrate with a melting point of 210° to 212° C. and a specific rotation in water of −26° (yield 93%).

The still impure l-glaucine-d-bitartrate was reacted with an aqueous solution of sodium hydroxide and extracted with ether. After evaporating the solvent, the residue was dissolved in 50 ml of ethyl alcohol and reacted with a solution of 1.15 of d-tartaric acid in 50 ml of ethyl alcohol. After separation there was obtained 3.39 g of l-glaucine-d-bitartrate showing a melting point of 212° to 215° C. and a specific rotation in water of −32°. The specific rotation of the l-glaucine base in ethyl alcohol was −101° (94% optical purity).

2.48 g of l-glaucine was reacted in 15 ml of ethyl alcohol with a small excess of 48% hydrobromic acid. After separation there was obtained 2.78 g of l-glaucine hydrobromide with a melting point of 235° C. (with decomposition) (yield 98.5%).

From the mother liquors of the first and second d-bitartrate crystallization there was obtained, after evaporation, a greenish residue, which was dissolved in 20 ml of water, treated with aqueous sodium hydroxide and then extracted with 250 ml of ether. After drying and filtering, the solvent was evaporated, giving 1.67 g of d-glaucine with a melting point of 120° C. The specific rotation in alcohol was 104.6°. By reacting this product with hydrobromic acid there was obtained a d-glaucine hydrobromide with a melting point of 235° C. (with decomposition). The d-glaucine obtained by methylation from d-boldine showed a specific rotation in ethyl alcohol of +115°.

EXAMPLE 6

To make l-glaucine hydrochloride, a quantity of l-glaucine was dissolved in a little methyl alcohol and to the solution there was added a small excess of concentrated hydrochloric acid. To the resulting voluminous precipitate there was added ethyl acetate, giving whitish to pink crystals. After filtering, washing with acetone and drying there were obtained white to pink fine crystals of l-glaucine hydrochloride with a melting point of 232° to 233° C.

EXAMPLE 7

For making l-glaucine hydroiodide, a quantity of l-glaucine was dissolved in 2 n hydrochloric acid and the solution reacted with saturated potassium iodide solution. The resulting crystalline precipitate was recrystallized from a mixture of methyl alcohol and ether. This gave a crystalline, yellowish glaucine hydroiodide with a melting point of 238° C.

EXAMPLE 8

A mixture of 3.92 g (0.01 Mol) of glaucine, 1.5 g (0.011 Mol) of potassium carbonate and 5 ml of methyl iodide was heated for 6 hours in methanol. The still hot solution was filtered and the solvent removed under vacuum, giving 4.2 g of d-glaucine methiodide with a melting point of 218° to 220° C. (yield 85%).

EXAMPLE 9

45 g (0.126 Mol) of laudanosine was dissolved in methanol and heated with 15 ml of methyl iodide for 2 hours under reflux. The resulting solid residue was filtered, washed and dried, giving 56 g of laudanosine methiodide monohydrate with a melting point of 238° to 240° C.

EXAMPLE 10

30 g of laudanosine methiodide hydrate was dissolved in 150 ml of 48% hydrobromic acid and heated under reflux for 15 hours. The resulting, yellow precipitate was filtered and dried, giving 22.1 g of laudanosoline methobromide with a melting point of 237° to 239° C.

EXAMPLE 11

50 g (0.0125 Mol) of laudanosoline methobromide was dissolved in 500 ml of water at 20° C. and reacted with a filtered aqueous solution containing 40.5 g of iron (III) chloride in 500 ml of water. After 24 hours there was added to the dark violet solution 500 ml of concentrated HCl. The mixture was evaporated down to about half its original volume. After adding methanol a yellow precipitate crystallized out. The product was 27.6 g of tetrahydroxyaporphine methochloride with a melting point of 236° to 239° C. (yield 63%).

The resulting product, and also the previously obtained products, were identified by ultra-violet, infrared and NMR spectra and by their melting points.

EXAMPLE 12

Coated pills with anti-thrombotic effect and the following compositions were made:

| Core: | l-glaucine hydrobromide | 100 mg |
|---|---|---|
| | lactose | 20 mg |
| | starch | 10 mg |
| | talcum | 10 mg |
| Coating: | gum arabic | 4.5 mg |
| | talcum | 35 mg |
| | crystallized sugar | 80 mg |
| | red pigment | 0.4 mg |
| | white wax | 0.1 mg |
| | | 120 mg |

EXAMPLE 13

For making capsules with long-period anti-thrombotic effect, stretch-capsules of hard gelatin were each filled with 160 mg of a mixture of the following components:

| d,l-glaucine hydrochloride | 60 mg |
|---|---|
| d,l-glaucine embonate | 100 mg |
| lactose | 20 mg |
| starch | 15 mg |
| magnesium stearate | 5 mg |
| | 200 mg |

EXAMPLE 14

For making a medicine intended for injection, ampoules were filled with a solution having the following composition:

| tetrahydroxyaporphine hydrochloride (corresponding to 1 mg of tetrahydroxyaporphine base) | 11.22 mg |
|---|---|
| sodium bisulphite | 0.7 mg |
| tartaric acid | 5.01 mg |
| sodium hydrogen tartrate | 10.2 mg |
| propylene glycol | 300 mg |
| distilled water | to 1 ml. |

EXAMPLE 15

Although the active compounds used according to the invention have an anti-thrombotic effect already in small dosages, the exact amount of active agent to be used in an anti-thrombotic tablet, dragee or capsule will vary with the severity of the thrombogenic risk of the patient, his weight and his response to the active compound. The active compound shall preferably be compounded with non-toxic edible excipient chemically inert to the active compound. The amount of excipient should preferably be sufficient to separate the particles of the active agent from each other and to cause quick solution or dispersion in the gastric juices in the stomach. To this purpose the composition may comprise about 10 to 99%, preferably 20 to 75% of active agent, the rest being carrier material and conventional adjuvants. Suitable excipients are lactose, sucrose, starch, talcum, stearic acid and its salts, and other commonly used excipients for tabletting and granulation and mixtures thereof.

For preparing anti-thrombotic tablets there were used the following ingredients:

| tetrahydropapaveroline hydrobromide | 100.0 mg |
|---|---|
| sucrose | 25.9 mg |
| starch | 22.1 mg |
| acacia | 7.8 mg |
| talc | 3.1 mg |
| magnesium stearate | 1.5 mg |
| stearic acid | 1.6 mg |
| | 162.0 mg |

The tetrahydropapaveroline hydrobromide may be substituted by an equal weight of any other active derivative described herein. The active compound was mixed with the sucrose and the gum acacia, and then with the starch made previously into a paste with a small amount of distilled water. This mixture was dried, converted into a granular powder and then blended with the talc, magnesium stearate and the stearic acid which act as mold lubricants. After mixing in a pony mixer the mixture was tabletted on a conventional tabletting machine.

EXAMPLE 16

There were prepared anti-thrombotic capsules each containing:

| tetrahydroxyaporphine hydrochloride | 400.0 mg |
|---|---|
| magnesium stearate | 4.0 mg |
| | 404.0 mg |

EXAMPLE 17

There were prepared anti-thrombotic tablets each containing:

| l-glaucine hydrobromide | 200.0 mg |
|---|---|
| magnesium stearate | 2.0 mg |
| | 202.0 mg |

EXAMPLE 18

In a conventional tabletting machine there were prepared antithrombotic tablets each containing:

| d,l-glaucine hydrobromide | 200.0 mg |
|---|---|
| polyvinylpyrrolidone | 15.0 mg |
| corn starch | 20.0 mg |
| | 235.0 mg |

Alternatively there can be prepared tablets adapted to be subsequently cut, each containing 400 mg active compound.

EXAMPLE 19

For making anti-thrombotic capsules hard gelatine capsules were each filled with a mixture of:

| d,l-glaucine hydrobromide | 200.0 mg |
|---|---|
| silicagel | 10.0 mg |
| magnesium stearate | 2.0 mg |
| | 212.0 mg |

COMPARATIVE TESTS

The effectiveness of several compounds corresponding to Formula (I) in influencing the aggregation of blood platelets in platelet-rich human blood plasma was compared with the effectiveness of papaverine hydrochloride. For this purpose highly diluted solutions were prepared of the active substances in physiological NaCl solution, the solutions showing definite molar concentrations. 10 microliters of each solution was tested, after 5 minutes incubation at 37° C., for its effect on aggregation of the blood platelets under the influence of adenosine diphosphate added to give the critical concentration. The measurements were made by the turbidity method described by Born in "Nature" (1962) on page 927. The critical concentration is the least concentration of adenosine diphosphate which results in primary aggregation of the blood platelets. This is followed by an irreversible secondary aggregation. The following table shows the results:

| Compound | Aggregation inhibition at $5 \times 10^{-6}$ molar concentration. |
|---|---|
| papaverine hydrochloride | − |
| tetrahydropapaverine hydrochloride | + |
| tetrahydropapaveroline hydrochloride | + |
| laudanosine methiodide | + |
| laudanosoline hydrobromide | + |
| laudanosoline methobromide | + |
| tetrahydroxyaporphine hydrochloride | + |
| tetrahydroxyaporphine methochloride | + |
| d,l-glaucine hydrobromide | + |
| l-glaucine hydrobromide | + |

COMPARATIVE TEST 2

Three active compounds, namely d,l-glaucine hydrobromide, tetrahydropapaveroline hydrobromide and tetrahydroxyaporphine hydrochloride were selected for in vivo assessment of the anti-thrombotic activity using a modified hamster cheek pouch technique described by Duling, Berne and Born (1968) and Begent and Born (1970).

Male golden hamsters, weighing 80–120 g, were anaesthetised with intraperitoneal pentobarbitone. The cheek pouch was everted using a cotton bud and spread out over a special Perspex stage. The top layer and connective tissue were removed leaving a thin vascular membrane which was transilluminated from below. The preparation was observed using a Leitz Dialux microscope and long working range objectives at a magnification of ×250. The cheek pouch remained in good condition for the duration of the experiment by continually bathing with Tyrode solution at a temperature of 37° C.

A micropipette of tip diameter 1–2 μm was filled with a 0.01 M solution of the sodium salt of adenosine diphosphate in distilled water. The micropipette was manipulated close to a venule of diameter 16–40 μm. The reference electrode was placed in contact with the animal. When the negative potential was applied from the external circuit the resultant current of approximately 300 nA ejected adenosine diphosphate (of the order of $2 \times 10^{-14}$ moles/sec) from the pipette. This caused the formation of a white body (platelet thrombus) at the tip of the pipette or slightly downstream. The growth rate of the thrombus was quantified by noting the time taken for 30%, 50% and 90% of the white body to form. When the current was switched off the white body rapidly embolized and no new white bodies could be formed until the current was reapplied.

In this study the effect of each drug was assessed over a period between 30 and 90 minutes after oral administration of each drug at the dose levels of 2, 5, 10 and 20 mg/kg.

Each compound was tested at four dose levels in 5 animals each with one group of 5 animals serving as a control. Preparation of the cheek pouch commenced at 15 minutes after dosing and thrombus stimulation commenced at 30 minutes after dosing each animal.

The growth rates were calculated as gradients of the regression lines by a standard program in a 9100B Hewlett Packard calculator. Dose response curves are obtained by plotting maximum inhibition expressed in percent of control group on thrombus induction in the micro-circulation of the hamster cheek pouch against the dose level. All three compounds were shown to inhibit thrombus formation when administered orally. The results are shown in the following table:

TABLE

| Product | oral dose for maximal inhibition mg/kg | maximal inhibition % | time of maximal inhibition min (after dosing) |
|---|---|---|---|
| glaucine hydrobromide | 50 | 41 | 60–70 |
| tetrahydropapaveroline hydrobromide | 5 | 40 | 50–60 |
| tetrahydroxyaporphine hydrochloride | 20 | 29 | 50–60 |

The dose response curves indicated that all compounds were active at relatively low dose levels and the inhibitory capacity of each compound tended to plateau at approximately 10 mg/kg.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method for inhibiting platelet aggregation, which comprises administering to a patient in need of such treatment a composition comprising a physiologically acceptable solid or aqueous liquid carrier and a platelet aggregation inhibiting amount of at least one active compound selected from the group consisting of:
   (a) tetrahydroxyaporphine,
   (b) glaucine containing 50 to 100% l-glaucine, and
   (c) the physiologically acceptable salts and N-alkyl ammonium salts of said compounds.

2. A method as defined in claim 1, wherein the active agent is selected from glaucine containing 50 to 100% l-glaucine and the physiologically acceptable salts and N-alkyl ammonium salts thereof having 1 to 4 carbon atoms in the N-alkyl group.

3. A method as defined in claim 1, comprising administering the composition in oral dosage unit form, each dosage unit containing between 100 and 800 mg of active agent.

4. A method as defined in claim 1, comprising administering the composition in form of a pill, dragee, tablet or capsule each containing between 100 and 500 mg of active agent.

5. A method as defined in claim 1, comprising injecting a composition containing a physiologically acceptable aqueous liquid carrier and between 10 and 200 mg of active agent per ml.

* * * * *